United States Patent
Cormier et al.

(10) Patent No.: US 6,537,264 B1
(45) Date of Patent: Mar. 25, 2003

(54) DEVICE AND METHOD FOR ENHANCING TRANSDERMAL FLUX OF AGENTS BEING SAMPLED

(76) Inventors: Michel J. N. Cormier, 278 Andsbury Ave., Mountain View, CA (US) 94043; Felix Theeuwes, 27350 Altamont Rd., Los Altos Hills, CA (US) 94022

(*) Notice: Subject to any disclaimer, the term of this patent is extended or adjusted under 35 U.S.C. 154(b) by 0 days.

(21) Appl. No.: 09/466,819

(22) Filed: Dec. 16, 1999

Related U.S. Application Data (63) Continuation-in-part of application No. 08/877,155, filed on Jun. 17, 1997, now abandoned.
(60) Provisional application No. 60/019,990, filed on Jun. 18, 1996.

(51) Int. Cl.[7] .................. A61M 31/00; A61B 5/00
(52) U.S. Cl. .................. 604/506; 600/575
(58) Field of Search .................. 604/21, 20, 264, 604/272, 890.1, 175, 239, 73, 506; 607/120, 126–128, 130, 131, 152; 600/575

(56) References Cited

U.S. PATENT DOCUMENTS

| | | | |
|---|---|---|---|
| 3,814,097 A | * 6/1974 | Ganderton et al. | 128/268 |
| 3,964,482 A | 6/1976 | Gerstel et al. | 128/260 |
| 4,127,118 A | * 11/1978 | Latorre | 128/79 |
| 4,287,819 A | 9/1981 | Enerit | 99/472 |
| 4,753,651 A | * 6/1988 | Eckenhoff | 604/896 |
| 4,941,517 A | * 7/1990 | Galloway | 141/1 |
| 5,054,499 A | 10/1991 | Swierczek | 128/770 |
| 5,122,114 A | * 6/1992 | Miller et al. | 604/49 |
| 5,161,532 A | 11/1992 | Joseph | 128/635 |
| 5,201,324 A | 4/1993 | Swierczek | 128/770 |
| 5,231,993 A | 8/1993 | Haber et al. | 128/770 |
| 5,250,023 A | 10/1993 | Lee et al. | 604/20 |
| 5,279,543 A | 1/1994 | Glikfeld et al. | 604/20 |
| 5,279,544 A | 1/1994 | Gross et al. | 604/20 |
| 5,300,110 A | * 4/1994 | Latterell et al. | 607/130 |
| 5,320,607 A | 6/1994 | Ishibashi | 604/115 |
| 5,368,047 A | 11/1994 | Suzuki et al. | 128/765 |
| 5,417,206 A | 5/1995 | Kaneyoshi | 128/632 |
| 5,441,490 A | 8/1995 | Svedman | 604/289 |
| 5,484,399 A | * 1/1996 | DiResta et al. | 604/21 |
| 5,582,184 A | 12/1996 | Erickson et al. | 128/763 |
| 5,682,233 A | 10/1997 | Brinda | 356/246 |
| 5,746,217 A | 5/1998 | Erickson et al. | 128/760 |
| 5,800,378 A | * 9/1998 | Edwards et al. | 604/22 |
| 5,820,570 A | 10/1998 | Erickson et al. | 600/573 |
| 5,879,326 A | * 3/1999 | Godshall et al. | 604/51 |
| 5,885,211 A | 3/1999 | Eppstein et al. | 600/309 |
| 6,022,316 A | * 2/2000 | Eppstein et al. | 600/309 |

FOREIGN PATENT DOCUMENTS

| | | | |
|---|---|---|---|
| EP | 0 497 620 | * 5/1992 | |
| WO | WO 97/07734 | 3/1997 | A61B/5/00 |
| WO | WO 98/00193 | * 8/1998 | |

* cited by examiner

*Primary Examiner*—Sharon Kennedy
(74) *Attorney, Agent, or Firm*—Owen Bates (57) ABSTRACT

A minimally invasive transdermal agent sampling device (2, 10) comprises a sheet (6) having a plurality of openings (8) and a plurality of microblades (4) for piercing the skin (20). A suction device (10) applies a negative pressure through the openings (8) to the microslits in the skin (20) for enhanced efflux of interstitial fluid. The device (2, 10) can be used for transdermal sampling of body analytes such as glucose for measuring/estimating blood glucose concentration.

17 Claims, 6 Drawing Sheets

DEVICE AND METHOD FOR ENHANCING TRANSDERMAL FLUX OF AGENTS BEING SAMPLED

CROSS REFERENCE TO RELATED APPLICATIONS

This is a continuation-in-part of U.S. patent application Ser. No. 08/877,155 filed Jun. 17, 1997, now abandoned which claims priority from a provisional U.S. patent application, Ser. No. 60/019,990 filed Jun. 18, 1996.

FIELD OF THE INVENTION

The present invention relates to transdermal agent sampling. More particularly, this invention relates to the transdermal sampling of agents, such as glucose, body electrolytes and substances of abuse, such as but not limited to alcohol and illicit drugs. The present invention uses skin-piercing microblades to enhance the transdermal flux of the agents during transdermal sampling.

BACKGROUND OF THE INVENTION

Obtaining a droplet of blood for the purpose of sampling a constituent (e.g., glucose) is commonly achieved by piercing the skin using a lancet or other blade-like element. Many such skin piercing devices are spring-driven so that the piercing is accomplished automatically by a pen or similar spring-loaded device. See for example, Suzuki et al. U.S. Pat. No. 5,368,047.

Many blood sampling devices also apply suction to the wound following piercing by the lancet. The suction assists in obtaining a blood sample of appropriate size for testing blood components such as glucose. See for example, Suzuki et al. U.S. Pat. No. 5,368,047; Swierczek U.S. Pat. No. 5,054,499; Ishibashi U.S. Pat. No. 5,320,607; Haber et al., U.S. Pat. No. 5,231,993; and Swierczek U.S. Pat. No. 5,201,324.

A partial vacuum applied to the skin has also been used in order to create suction blisters wherein the upper epidermis layer of the skin is separated from the dermis layer of the skin. To separate the epidermis from the dermis, a partial vacuum of about 0.25 atm (200 mm Hg) is applied for a period of about 2 hours. Upon separation of the epidermis from the dermis, The epidermis layer is then pierced or removed thereby exposing the underlying dermis layer for subsequent enhanced transdermal delivery of therapeutic agents such as drugs. See for example, Svedman, U.S. Pat. No. 5,441,490.

A partial vacuum has also been used in order to determine blood gas content by applying the partial vacuum to intact skin. The partial vacuum causes "suction effusion fluid" to appear on the skin surface and vaporization of blood gases therefrom. See for example, Kaneyoshi, U.S. Pat. No. 5,417,206.

There have been many attempts to enhance transdermal flux by mechanically puncturing the skin prior to transdermal drug delivery. See for example U.S. Pat. Nos. 5,279,544 issued to Gross et al., U.S. Pat. No. 5,250,023 issued to Lee et al., and U.S. Pat. No. 3,964,482 issued to Gerstel et al. These devices utilize tubular or cylindrical structures generally, although Gerstel does disclose the use of other shapes, to pierce the outer layer of the skin. Each of these devices provide manufacturing challenges, limited mechanical attachment of the structure to the skin, and/or undesirable irritation of the skin.

In addition to sampling blood, attempts have been made to sample interstitial fluid and to correlate the analyte content in the interstitial fluid with that in the blood. See for example, Joseph, U.S. Pat. No. 5,161,532; Erickson et al., U.S. Pat. No. 5,582,184; Brinda, U.S. Pat. No. 5,682,233; Erickson et al., U.S. Pat. No. 5,746,217 and Erickson et al., U.S. Pat. No. 5,820,570. One of the advantages of sampling interstitial fluid is that the wound created in the skin is not as deep as the wound needed for a blood sampling. Thus, interstitial fluid sampling is generally considered less invasive than blood sampling.

However, there is still a need for even less invasive sampling of interstitial fluid for the purpose of determining analyte concentrations in the blood, for example, blood glucose concentrations. Unfortunately, less invasive techniques tend to draw smaller and smaller fluid samples making accurate analyte concentration analysis problematic.

DESCRIPTION OF THE INVENTION

The present invention provides a reproducible, high volume production, low-cost device suitable for transdermal analyte sampling. The invention comprises a plurality of microblades for piercing the skin. The microblades typically have a length of less than about 0.4 mm and a width and thickness which is even smaller. In spite of their small size, the microblades can be made with an extremely reproducible size and shape so that the microslits formed by the microblades puncturing the skin also have a very reproducible size and depth. Because the microblades have a small thickness (i.e., small relative to the width and length of the microblade), the microblades produce less tissue damage for a given cross-section than a skin piercing microneedle having a circular cross-section. The device of the present invention pierces the stratum corneum of a body surface to form pathways through which a substance (e.g., a body analyte such as glucose) can be withdrawn (i.e., sampled). The device of the present invention is used in connection with body analyte or drug sampling. The sampling device used with the present invention is a negative pressure driven device which applies a partial vacuum (also referred to herein as "negative pressure") to the microslit skin. The negative pressure causes interstitial fluid to efflux from the micrcoslits. The interstitial fluid is collected and analyzed for content and/or concentration of a body analyte such as glucose.

In one aspect of the invention, the device comprises a sheet having a plurality of openings therethrough, and a plurality of microblades integral therewith and extending downward therefrom. The negative pressure driven device applies negative pressure (i.e., suction) to the microslits through the openings in the sheet.

The device is optionally anchored to the body surface in any of a plurality of ways, including but not limited to, prongs or barbs on the microblades, and skin-contact adhesives.

MODES FOR CARRYING OUT THE INVENTION

Figure 1:
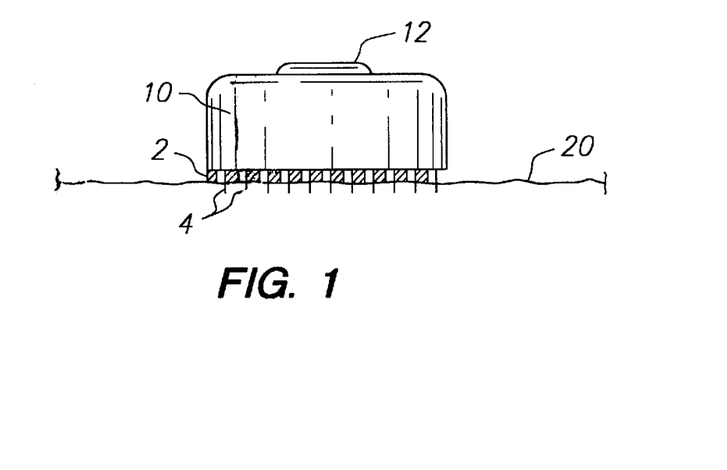
FIG. 1 is a side view of one embodiment of a negative pressure driven device with a microblade array shown in section according to one embodiment of the present invention.

Turning now to the drawings in detail, one embodiment of the microblade array device 2 of the present invention is generally shown in FIG. 1 for use with negative pressure driven device 10. Device 10 and device 2, in combination, are used for the percutaneous sampling of an agent. Device 10 is a known negative pressure (i.e., suction) applying device such as that disclosed in Ishibashi, U.S. Pat. No. 5,320,607, the disclosures of which are incorporated herein by reference. Device 10 is mounted on the skin distal surface of device 2. The skin proximal side of device 2 is in contact with, and preferably anchored to, the surface of skin 20, with the microblades 4 extending at least through the stratum corneum layer of skin 20. By appropriately sealing the device 10 against the skin distal side of device 2, the negative pressure applied by device 10 causes suction to be applied through the openings 8 in sheet 6. In this manner, interstitial fluid is extracted out of the microslits cut in the skin 20 and drawn into device 10. The negative pressure driven sampling device 10 can optionally include an agent sensing element (not shown in the figures). The optional agent sensing element can be any of a variety of chemically reactive sensors and indicators, for example the color indicating test strips used with glucose testing. The device 10 can have a cut out or transparent widow in the area of the indicators so that the indicators can be readily viewed.

The terms "substance" and "agent" are used interchangeably herein and broadly include substances such as glucose, electrolyte, alcohol, illicit drugs, etc. that can be sampled through the skin. The major barrier properties of the skin, such as resistance to substance efflux, reside with the stratum corneum. The inner division of the epidermis generally comprises three layers commonly identified as stratum granulosum, stratum Malpighi, and stratum germinativum. There is substantially less resistance to permeation through the underlying stratum granulosum, stratum Malpighi, and stratum germinativum layers than the resistance to permeation through the stratum corneum. The device of the present invention is used to form microslits in the stratum corneum and produce a percolation area in the skin for improved transdermal sampling of an agent.

Figure 2:
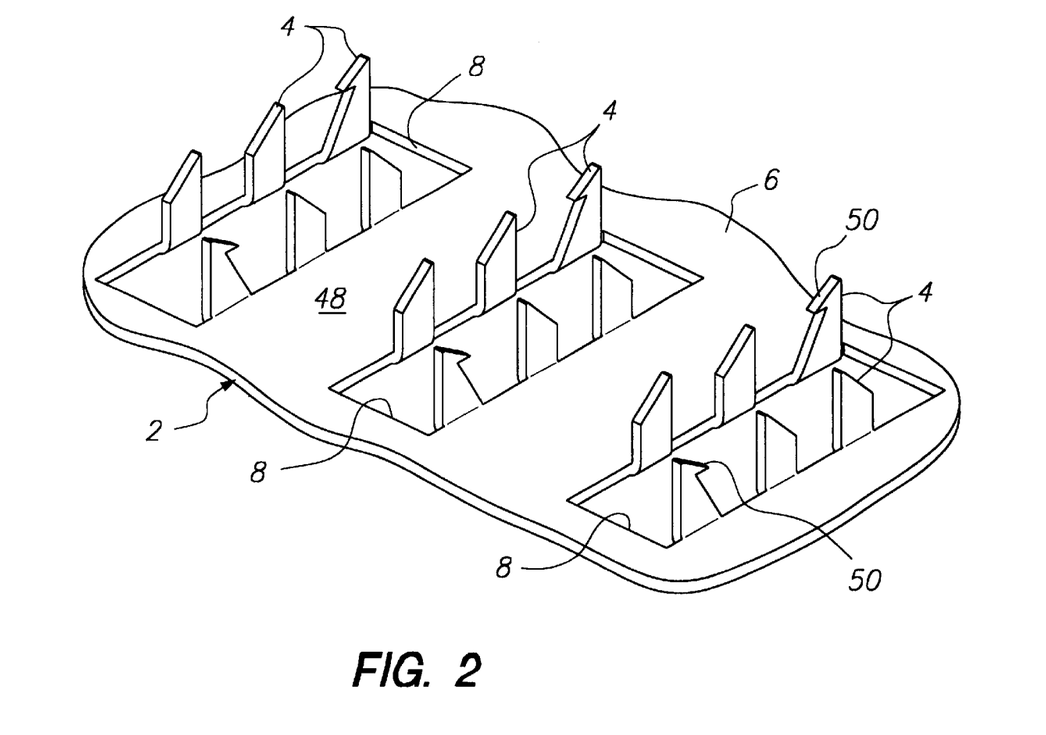
FIG. 2 is an enlarged perspective view of the skin proximal side of the microblade array device in accordance with one embodiment of the present invention.

Device 2 comprises a plurality of microblades 4 (i.e., a microblade array) extending downward from one surface of a sheet or plate 6 (see FIG. 2 in which device 2 is in an inverted position to show the microblades). The microblades 4 penetrate the stratum corneum to the epidermis when pressure is applied to the device to increase the sampling of a substance through the skin. The term "body surface" as used herein refers to the skin of an animal, particularly a human.

Preferably, the device 2 of the present invention helps to keep the device attached to the skin so that the percolation areas and a continuous pathway are preserved during movement of the body surface. In the embodiment shown in FIG. 2, projections in the form of barbs 50 on at least one of the microblades 4 assist in anchoring the device 2 and any corresponding negative pressure driven device or structure used in combination therewith to the skin. Barbs 50 can be on any number of the microblades from one microblade to all microblades. Other embodiments which assist to anchor the device to the skin will be discussed below.

The microblades 4 are generally formed from a single piece of material and are sufficiently sharp and long for puncturing the stratum corneum of the skin. In one embodiment, the microblades 4 and the sheet 6 are essentially impermeable or are impermeable to the passage of an agent. The sheet 6 is formed with an opening 8 between the microblades 4 for enhancing the movement of an agent therethrough. In the case of agent (e.g., body analyte) sampling, the analyte (or interstitial fluid containing the analyte) migrates from the body through the microslits in the stratum corneum which are cut by the microblades 4. In one embodiment, the opening 8 corresponds to the portion of the sheet 6 occupied by each of the microblades prior to the microblades being transpositioned into the downward depending position. The number of microblades 4 per opening 8 can be any number, preferably however between 1 and about 30 microblades per opening. Furthermore, the number of openings per device and the number of microblades per device are independent. The device 2 has a microblade density of at least about 10 microblades/cm$^2$ and less than about 1000 microblades/cm$^2$, preferably at least about 50 microblades/cm$^2$, more preferably at least about 100 microblades/cm$^2$, and still more preferably at least about 150 microblades/cm$^2$. In similar fashion, the number of openings per unit area through which the agent passes, is at least about 10 openings/cm$^2$ and less than about 1000 openings/cm$^2$, preferably about 100 to 500 openings/cm$^2$. The present invention produces a percolation area of about 0.005 to 0.05 cm$^2$/cm$^2$ of body surface, preferably about 0.01 cm$^2$/cm$^2$ of body surface.

As is best shown in FIG. 2, the microblades 4 have a thickness which is much smaller than the width of the microblades near their base, i.e., near the point where the microblades are attached to the plate 6. This microblade geometry provides maximum agent percolation area with a minimum microblade penetration area, and hence less tissue damage. The agent percolation area is the skin area in contact with the microblades, which provides for agent efflux from the skin. The microblades are shaped with the largest possible surface area with a minimal cross-sectional area so as to give the largest possible percolation area. Thin microblades are better than round protrusions for this purpose because for the same cross-section, a thin microblade produces more percolation area and less tissue damage than a round protrusion. This is a crucial advantage over the prior art round elements such as needles and tubes. Thin microblades also require less insertion force than round protrusions. The width of each microblade can be any of a range of widths. The widths can be different from microblade to microblade in the array pattern. Likewise, the width can be variable along the length of the microblade, as will be described in more detail below. The width of the microblade at the intersection of the microblade and the body surface after the microblade array has been inserted is preferably in the range of about 25 $\mu$m to about 500 $\mu$m, more preferably about 50 $\mu$m to about 400 $\mu$m, more preferably 100 $\mu$m to about 300 $\mu$m.

In one embodiment, the microblades 4 (FIG. 5) are also provided with slanted (i.e., angled) leading edges 64 to further reduce the insertion force required to press the microblades into the skin tissue. The angle of the leading edge is designated as $\alpha$. The slanted leading edges produce a cut through the skin tissue that is equal to the full width of the microblade 4 while reducing the amount of metal that is in the skin tissue. In other words, a flat leading edge (i.e., $\alpha$ is 90°) produces a microblade with a larger amount of microblade material in the skin tissue than is produced by a microblade having a slanted leading edge. The leading edges of each microblade can all be the same angle or can be at different angles as shown in FIG. 5. The angle a of each leading edge can be any angle between about 10° to 90°, preferably between about 10° to 60°, more preferably about 10° to 40°. The leading edge can also be segmented into two sections at different angles. For example, the first segment can have an angle a between about 10° to 40° and then transition to a second segment having an angle between 20° to 60°. Alternatively, the leading edge of each microblade can be arcuate (i.e., curved) in shape, having, for example, a convex or concave shape. In one embodiment, the leading edge is a curved tip across the entire width of the microblade.

The microblades 4 are formed using a photo-etching process which is described in detail hereinafter. This process allows the microblades 4 to be reproducibly formed on a very small (i.e., tens of microns) scale. This process also allows the microblades 4 to be formed in shapes which help anchor device 2 to the skin. In one embodiment, the microblades 4 are provided with barbs 50 (FIGS. 2, 3 and 5) in some fashion so that the device 2 and any corresponding sampling device attached thereto stays attached to the skin after being applied with pressure. The degree of attachment and the number and size of the barbs is such as to retain the negative pressure driven sampling device during the normal activity of the wearer, but not cause pain upon removal. As the microblades are pressed into the skin tissue for use, the leading edge 64 of each microblade cuts through and pushes aside the skin tissue. After the microblades have come to rest in the skin, the skin due to its elastic nature at least partially comes back together around the edges of the microblades, in this way the surface 66 on each microblade having a barb 50 engages skin tissue and anchors the device in the skin. If the microblade is left in the skin for an extended period of time (e.g., 24 hours), the skin tissue begins to heal together in the area behind the surface 66 of the barb thus improving the anchoring of the device. Only one barb per microblade is shown in the figures but it is within the scope of the present invention that each microblade can have a plurality of barbs extending therefrom. The microblades, in one embodiment, have a cross-section that is wider in the area of the skin distal end of the microblade than in the area of the skin proximal end, thus providing additional anchoring of the distal end in the skin. For example, the microblades can have an "arrowhead" shape. Furthermore, the barbs 50 shown in the figures are in the same plane as the microblade, however the barbs can be oriented outside of that plane for example by a separate bending step or by using a shaped punch and die to produce a curve in the microblade and barb. Curving the tips of the microblade outside the plane of the microblade generally provides better anchoring. Insertion of such microblades causes the barbs to curve in the curve direction but retraction causes them to return to their prior position. The resulting curved cross-section of the microblade can be, but is not limited to, angular, semi-circular, C-shaped, or banana-shaped to effect a larger cross-section of openings in the skin.

The plurality of microblades 4 for puncturing the stratum corneum are present on one face surface 48 of the device 2 in any predetermined arrangement, for example, as a cluster of microblades spaced in rows having any desired number, or in any spaced apart relation of one microblade to each other. The device 2 of the embodiment shown in FIGS. 1 and 2 is produced by the pattern shown in FIG. 3. Each microblade has a width and thickness that facilitates penetration of the stratum corneum without bending. In the embodiment of FIG. 3, there are six microblades 4 in each opening 8 in sheet 6. Each opening 8 in this embodiment is 1 mm long and 300 $\mu$m wide. Correspondingly, the width of each microblade is between about 137.5 $\mu$m to about 175 $\mu$m and the length is about 250 $\mu$m. The required length of the microblades is subject to variation of the body surface being penetrated and corresponds to the natural thickness of the stratum corneum, for one of the principle features of the invention is that the microblades are to penetrate the stratum corneum into the epidermis. Another factor affecting microblade length is the method of microblade application since the microblades frequently do not penetrate the skin to a depth equal to the microblade length due to the elastic properties of living animal skin. Usually, the microblades will be about 25 $\mu$m to about 500 $\mu$m in length, with the length for most applications being between about 100 $\mu$m to about 450 $\mu$m.

The pattern for any of the microblade array devices of the present invention are produced with a photo-etching process. A thin sheet or plate 6 of metal such as stainless steel or titanium is etched photo-lithographically with patterns containing microblade-like structures. In general, a thin laminate dry resist or wet resist is applied on a sheet about 7 $\mu$m to about 100 $\mu$m thick, preferably about 25 $\mu$m to about 50 $\mu$m thick. The resist is contact exposed using a mask having the desired pattern and is subsequently developed. These operations are conducted in much the same way that they are for the manufacture of a printed circuit board. The sheet is then etched using acidic solutions. After the pattern has been etched through the sheet, the sheet is placed on a die 52 (shown schematically in FIG. 8) having a plurality of openings 56 corresponding to the openings 8 in the sheet. A punch 54 having a plurality of protrusions 58 corresponding to the openings in the sheet and die is initially located above the sheet and die. At the initial stage, the microblades 4 are in the same plane as the rest of the sheet 6. The protrusions 58 on the punch 54 are then pressed into the openings 56, thus bending the microblades 4 downward to be at an angle (e.g., substantially perpendicular) to the plane of the sheet. The finished structure provides microblades 4 with an adjacent opening 8 for the passage of a substance therethrough when the device 2 is applied to the skin. Rectangular openings 8 are shown in the figures but the invention encompasses the use of any shape openings including, but not limited to, square, triangular, circular and elliptical.

Figure 4:
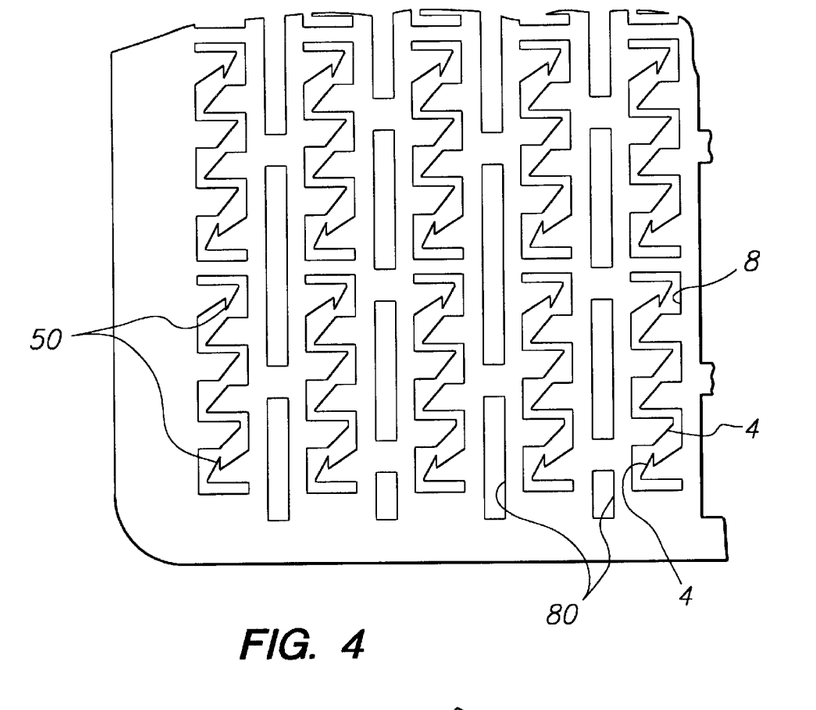
FIG. 4 is partial top plan view of yet another embodiment of the microblade array pattern of FIG. 3.
Figure 5:
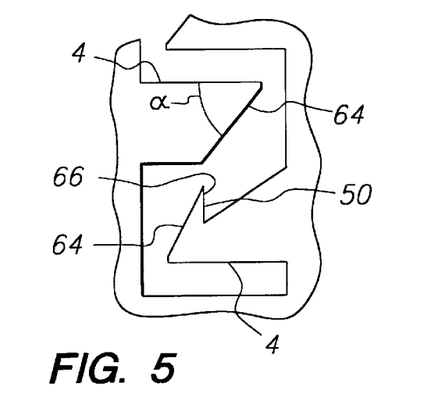
FIG. 5 is an enlarged view of a portion of the microblades of the microblade array pattern of FIG. 3.

The sheet 6 in some areas can have additional etched openings 80 (FIG. 4) to alleviate the curl created during punching and/or to provide for flexibility in the dense microblade array patterns because in some embodiments the sheet becomes very stiff after punching. The openings can be any of a variety of shapes (e.g., rectangular, circular, elliptical, triangular, etc.). The openings also allow the sheet to be more easily curved to match the curvature of the body surface to which it is to be attached which improves anchoring of the device. The present invention maximizes the openings through the sheet but with a sufficient number of horizontal and vertical continuous portions in the sheet to prevent the sheet from being too flexible (i.e., flimsy). If the openings are made too long in any one dimension, the sheet will bend (i.e., crinkle). In addition, it is also possible to treat the devices after punching with heat or plastic deformation such that the radius of curvature of the sheet becomes equal to or somewhat smaller than the curvature of the body, where it is to be attached to enhance anchoring. The concave surface can be shaped to match the convex pattern of the body.

Figure 6:
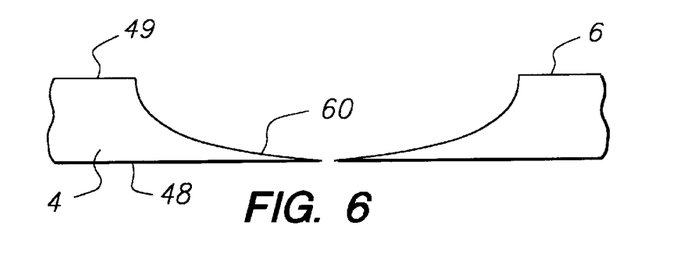
FIG. 6 is an enlarged view of a microblade tip in accordance with one embodiment of the present invention.
Figure 7:
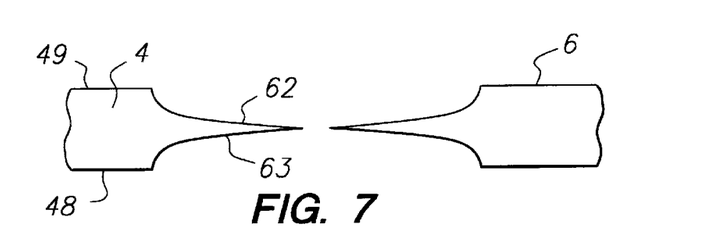
FIG. 7 is an enlarged view of a microblade tip in accordance with another embodiment of the present invention.
Figure 8:
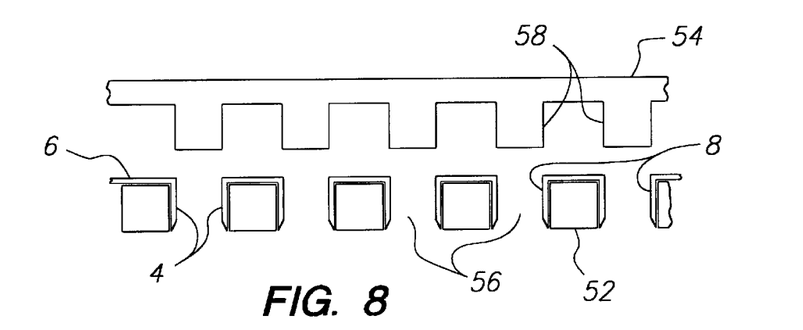
FIG. 8 is a diagrammatic representation of a method for producing microblades of the present invention from the microblade array pattern of FIG. 3.

The microblades 4 can be patterned with resist on both sides 48,49 and subsequently etched simultaneously from both sides (FIG. 7) to achieve maximum pattern resolution for a given sheet thickness and to produce a knife-like edge that can not be achieved with conventional stamping and punching processes. Alternatively, the microblades 4 can be patterned and etched from one side (i.e., side 49) only (FIG. 6). When etching from one side only, the etching process can be controlled to etch selective depths in the plate 6 along the length of the microblades (e.g., at the microblade tips) to produce a single angle 60 at the tip of the microblade which maximizes the sharpness of the knife-like edge of the microblade. In this embodiment, the lithography process produces a portion of the microblade that is thinner than the remainder of the thickness of the microblade and of the sheet. The lithography process also can produce very small dimensioned elements for the anchoring and the penetration aspects of the invention.

In another embodiment of the two-sided etching process, the microblade array pattern of any of the embodiments of the present invention is etched into the top surface 49 of sheet 6. A second pattern equivalent to the area bounded by each of the openings 8 (e.g., rectangular) is etched into the bottom surface 48 such that each of the microblades in the microblade array pattern is thinner than the surrounding sheet 6. As a result, the sheet 6 forms a strong base and as the punch 54 deforms the microblades 4 downward, each of the microblades plastically deforms so as to produce microblades that are straighter and more truly perpendicular to the sheet.

In one embodiment of the etching process, a dry resist (e.g., "Dynachem FL" available from Dynachem located in Tustin, Calif.) is applied 12.5 µm thick to one or both sides of the sheet and exposed in a standard manner. Then a suitable spray etcher (e.g., "Dynamil VRP 10/NM" available from Western Tech. Assoc. located in Anaheim, Calif.) is used to spray a mixture of ferric chloride and hydrochloric acid onto the resist and sheet at 52° C. (125° F.) for two minutes. A standard caustic stripper is used for the resist removal.

In another embodiment of the etching process, a wet resist (e.g., "Shipley 111S" available from Shipley Corporation, located in Marlborough, Mass.) is applied 7.5 µm thick at about 20° C. (70° F.) to one or both sides of the sheet and exposed in a standard manner. Then a suitable etchant (e.g., ferric chloride) is sprayed onto the resist and sheet at 49° C. (120° F.). A standard caustic stripper is used for the resist removal.

Figure 9:
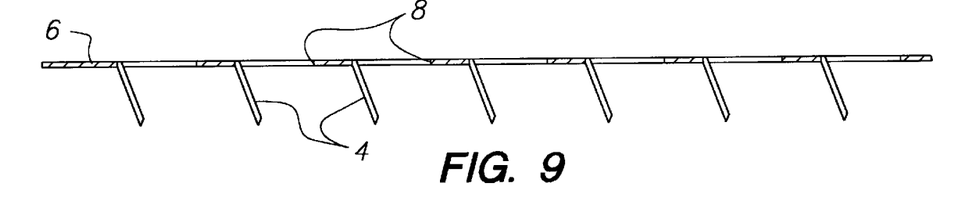
FIG. 9 is an enlarged cross-sectional view of angled microblades in accordance with one embodiment of the present invention.

Generally, the microblades 4 are at an angle of about 90° to the surface 48 of the sheet 6 after being punched, but they can be disposed at any angle forward or backward from the perpendicular position that will facilitate penetration of and optionally anchoring to the stratum corneum. In one embodiment (FIG. 9), the microblades are all aligned at an angle between about 1° and about 89° degrees, preferably about 10° to about 60°, more preferably about 20° to 45° to facilitate the device being slid along and into the skin. The angled microblades have two principal advantages. First, penetration of the microblades is not opposed by the elasticity of the skin because the microblades are slid horizontally into the skin as opposed to pressing vertically on the skin. Second, the angled microblades act to anchor the device in the skin as any motion of the skin is less likely to dislodge the microblades. In addition, other anchoring elements such as barbs, openings, etc. can be used with the angled microblades to further enhance anchoring of the device.

Figure 22:
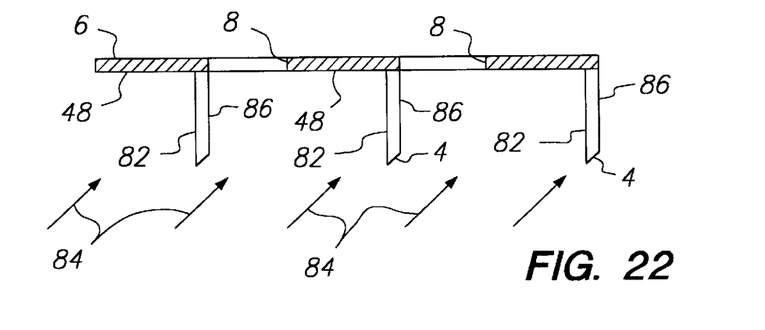
FIG. 22 is a diagrammatic cross-sectional view of another embodiment of the microblades of the present invention.

In one embodiment (FIG. 22), anchoring of the device is achieved by coating the surface 48 of sheet 6 and surface 82 of each microblade 4 with an adhesive. The adhesive can be sprayed on the device 2 along the direction indicated by arrows 84. In this embodiment, the agent is free to pass through the openings 8 and along surface 86 of each microblade unencumbered by the adhesive. It is also possible to apply the adhesive on only surface 48 and not on the microblade surfaces 82. This can be accomplished, for example, by applying the adhesive onto surface 48 after the microblades 82 have been punched by spraying the adhesive in a direction which is parallel to the axis of the microblades 82. It is further possible to apply the adhesive only on the surfaces of microblades 82 and not on the surface 48 of sheet 6 in order to anchor the device, although this last design is the least preferred adhesive anchoring means.

The sheet and microblades can be made from materials that have sufficient strength and manufacturability to produce microblades, such as, glasses, ceramics, rigid polymers, metals and metal alloys. Examples of metals and metal alloys include but are not limited to titanium, stainless steel, iron, steel, tin, zinc, copper, platinum, aluminum, germanium, nickel, zirconium, and titanium alloys consisting of nickel, molybdenum and chromium, metals plated with nickel, gold, rhodium, iridium, titanium, platinum, and the like. An example of glasses include a devitrified glass such as "Photoceram" available from Corning in Corning, N.Y. Examples of rigid polymers include but are not limited to polystyrene, polymethylmethacrylate, polypropylene, polyethylene, "Bakelite", cellulose acetate, ethylcellulose, styrene/acrylonitrile copolymers, stryrenetbutadiene copolymers, acrylonitrile/butadiene/styrene (ABS) copolymers, polyvinyl chloride and acrylic acid polymers including polyacrylates and polymethacrylates.

Figure 3:
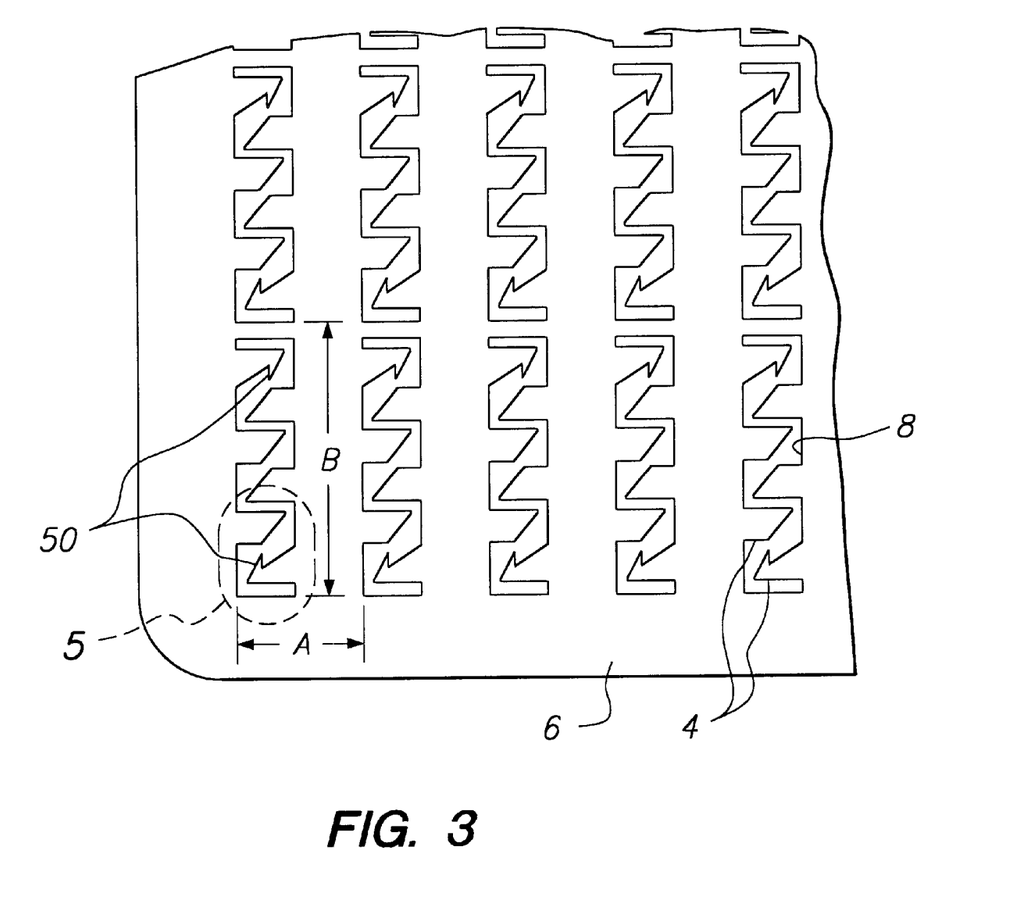
FIG. 3 is a partial top plan view of a microblade array pattern in accordance with one embodiment of the present invention for forming microblades with anchoring elements.

Very dense patterns can be created with unit cells wherein a unit cell has a width A and a length B as illustrated in FIG.

3. In one embodiment (not shown), the pattern has the following characteristics: a unit cell area of 0.63 mm by 3.8 mm; the lineal length of a cut in a unit cell is approximately equal to 15 mm; and the open skin length per square centimeter is 625 mm.

The microblades of the present invention make an elongated, thin microcut (i.e., a slit) in the skin surface because the microblades have a small thickness (relative to their width and length) resulting in a minimal microblade cross-sectional area for the portions of the microblades in the skin. The geometry of the microblades 4 results in minimal microblade volume in the skin with maximal microblade surface area in the skin. The advantages of the present invention include, but are not limited to: (1) the thin microblade geometry produces the maximum analyte percolation area for a given cross-section of the microblade; (2) minimal tissue damage occurs because the amount of microblade material in the skin and hence the volume loading is minimized; (3) slanted leading edges (or equivalent pointed shapes) further minimize the amount of volume loading or tissue damage while preserving a large percolation area; (4) for a given volume loading, the larger the surface area, the larger the frictional retaining force in the skin; and (5) for a given desired percolation area, there are fewer microblades necessary and therefore the force on each tip is higher making skin penetration easier.

Figures 10, 11, 12:
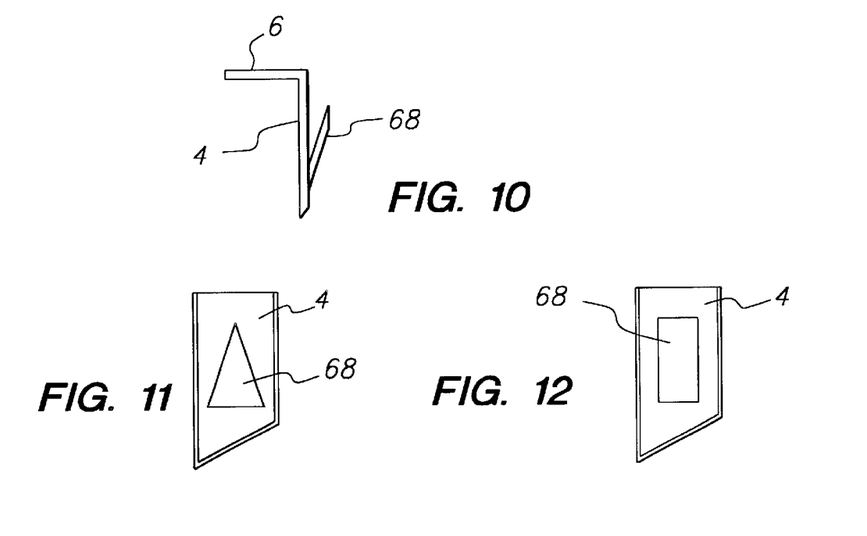
FIGS. 10, 11 and 12 are yet other embodiments of the microblades with anchoring elements of the present invention.
Figure 13:
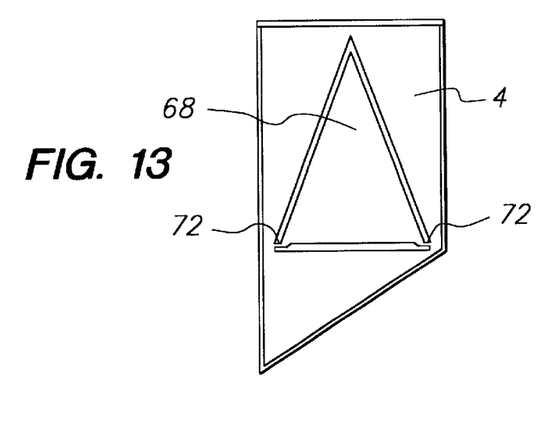
FIG. 13 is a right side elevational view of another embodiment of a microblade with an anchoring element.
Figure 14:
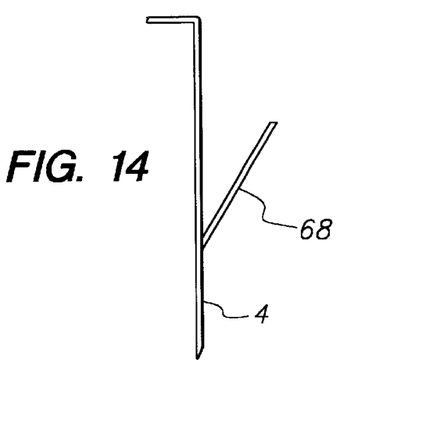
FIG. 14 is an end view of the microblade of FIG. 13.
Figure 15:
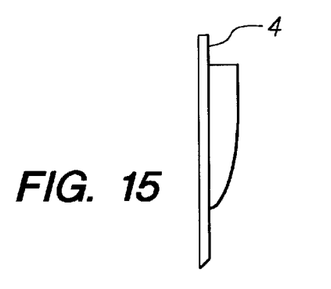
FIGS. 15 and 16 are another embodiment of the microblade and an anchoring element.
Figure 16:
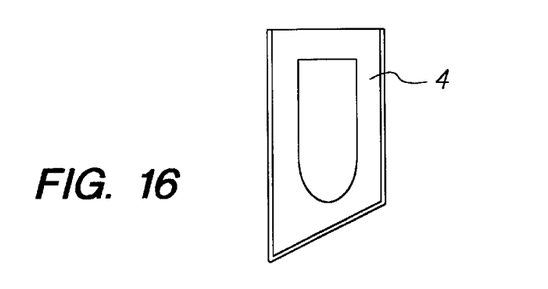

In other embodiments (FIGS. 10–16) other anchoring elements are used in the present invention. In the embodiments shown in FIGS. 10–14, prong 68 is etched in the side of some or all of the microblades 4, and punched lightly so as to protrude outward from the plane of each of the microblades, as illustrated in FIGS. 10 and 14. After the punching of the prongs, the microblades may be repunched to regain their substantially vertical orientation. Hinges 72 (FIG. 13) can be used to control the retention force of the barb for anchoring. The hinges allow for the retention force to be tailored independently of the size of the microblade because the force required to bend or punch the prong is set independently of the size of the microblades by the shape or size of the hinge. In other words, the force can be tailored by the amount of attachment of the prong to the plate, the greater the attachment, the greater the force.

Prongs may protrude from either side of the microblade, or both sides, if desired. The shape of each prong can be any of a variety of shapes such as triangular, square, etc. as shown in FIGS. 11 and 12. In another embodiment, a curved protrusion 70 (FIGS. 15 and 16) is made by etching a slit in some or all of the microblades followed by punching. The prongs and curved protrusions act to anchor the device in the skin similar to the manner described previously.

Figure 17:
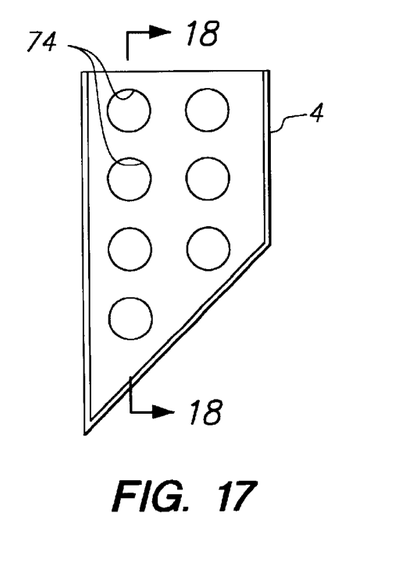
FIG. 17 is a right side elevation view of a microblade with anchoring elements in accordance with one embodiment of the present invention.
Figure 18:
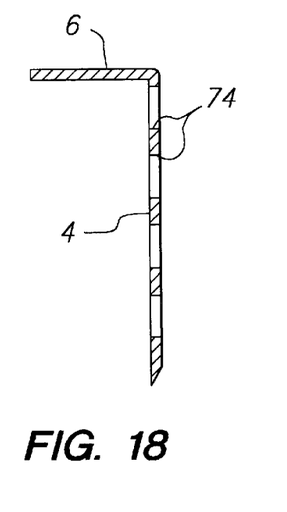
FIG. 18 is a cross-sectional view taken along line 18—18 of FIG. 17.
Figure 19:
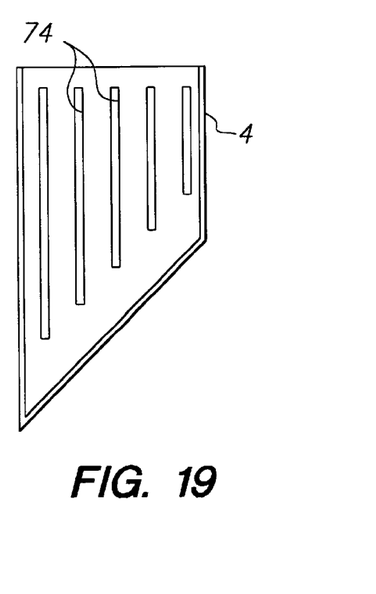
FIG. 19 is a right side elevational view of another embodiment of a microblade with an anchoring element.

In other embodiments other anchoring elements are used. In the embodiments of FIGS. 17–19, the microblade 4 has additional openings 74 extending through the microblade to enhance anchoring. The edges forming the holes or other linear openings are etched through the microblade. Alternatively, or in addition, numerous small pits (i.e., indentations) rather than holes can be etched in the surface of the microblade. As described above, the elastic nature of the skin tissue causes the skin to move into the openings or pits. In the embodiments with openings, the skin tissue may heal and reconnect through the openings to provide even greater anchoring.

Figure 20:
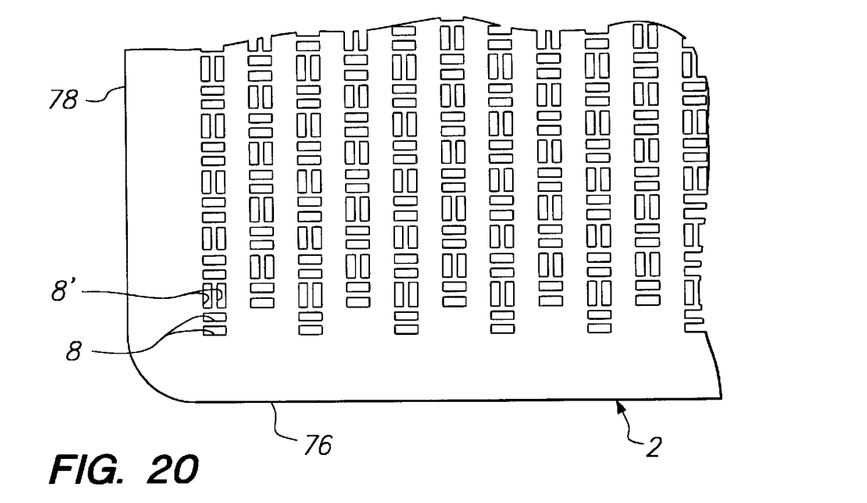
FIG. 20 is an enlarged partial top plan view of still another embodiment of the microblade array pattern.
Figure 21:
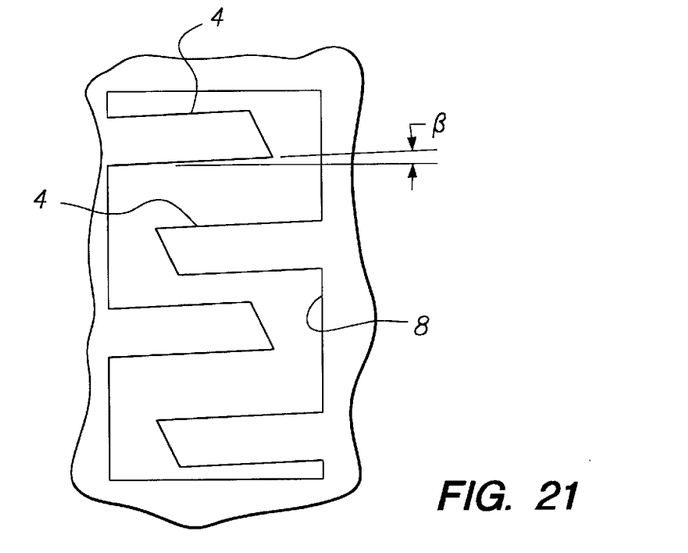
FIG. 21 is an enlarged partial top plan view of yet another embodiment of the microblade array pattern.

In a further embodiment (FIG. 20), a plurality of microblades in an opening 8 are arranged at 90° to another plurality of microblades in an opening 8' such that anchoring in two directions is obtained. In other words, the microblades (not shown) associated with the openings 8 are oriented parallel to the edge 76 of the device 2 and the microblades (not shown) associated with the openings 8' are oriented parallel to the edge 78 of the device. The microblades associated with each opening 8 can be oriented at any angle with respect to the microblades associated with each opening 8'. Alternatively, the microblades within each opening can be along perpendicular sides of the openings. In a similar manner, the microblades within each opening can be formed in a serrated pattern as illustrated in FIG. 21. This pattern allows the microblades to have different, controllable angles with respect to each other defined by the angle of the punch used and the etched angle β of the pattern.

The number of microblades and openings of any of the embodiments of the device 2 is variable with respect to the desired flux rate, agent being sampled, and the negative pressure driven sampling device used, and other factors as will be evident to one of ordinary skill in the art. In general, the larger the number of microblades per unit area (i.e., the microblade density), the more distributed is the flux of the agent through the skin because there are a greater number of agent-conveying pathways through the skin. Consequently, the smaller the number of microblades per unit area, the more concentrated is the flux of the agent through the skin because there are fewer pathways.

The device 2 of the present invention is used with a suction (i.e., negative pressure) applying device which can be used to transdermally sample interstitial fluid containing any of a variety of agents including, but not limited to glucose, body electrolytes, alcohol, blood gases, and illicit substances such as drugs of abuse. The sampling device can be attached to a body surface by means of a flexible adhesive overlay and the anchoring elements of device 2.

While the invention has been described in conjunction with the preferred specific embodiments thereof, it is to be understood that the foregoing description as well as the example are intended to illustrate and not limit the scope of the invention. Other aspects, advantages and modifications within the scope of the invention will be apparent to those skilled in the art to which the invention pertains.

What is claimed is:

1. A device for piercing the stratum corneum of a body surface to form pathways through which a substance can be withdrawn for sampling, comprising:

a sheet having a plurality of openings therethrough and a plurality of microblades extending downward therefrom; and a negative pressure sampling device which applies negative pressure to the pathways through the openings.

2. The device of claim 1, wherein the sampled substance is selected from the group consisting of body electrolytes, illicit drugs and glucose.

3. The device of claim 1, wherein the microblades have a length sufficient to pierce the stratum corneum of the body surface to a depth of at least about 25 μm.

4. The device of claim 1, wherein the sheet has at least about 10 microblades/$cm^2$.

5. The device of claim 1, wherein the sheet has at least about 10 openings/$cm^2$.

6. The device of claim 1, wherein the microblades are oriented approximately perpendicular to the sheet.

7. The device of claim 1, wherein the sheet and the plurality of microblades are composed of a material selected from the group consisting of metals, metal alloys, glasses, ceramics and rigid polymers.

8. The device of claim 1, wherein the sheet and the plurality of microblades are substantially impermeable to the passage of the agent.

9. The device of claim 1, wherein at least a portion of the plurality of microblades are located along a periphery of an opening through the sheet.

10. The device of claim 1, wherein at least a portion of the plurality of microblades are located along a periphery of a plurality of openings through the sheet.

11. The device of claim 1, wherein at least a portion of the plurality of microblades have a thickness in the range of about 7 µm to about 100 µm.

12. The device of claim 1, wherein at least a portion of the plurality of microblades have a thickness in the range of about 25 µm to about 50 µm.

13. The device of claim 1, including an anchor anchoring the sheet to the body surface.

14. The device of claim 13, wherein the anchor is selected from the group consisting:

(i) a projection extending out from the at least one microblade;

(ii) a barb;

(iii) at least one opening extending through the at least one microblade;

(iv) an adhesive on a body contacting surface of the sheet and on at least one surface of at least one of the plurality of microblades;

(v) each of the microblades having an axis, the microblades being oriented so that the microblade axes are substantially parallel and the axes form an angle of about 1° to about 89° relative to the sheet;

(vi) each one of the plurality of microblades defines essentially a plane and wherein the anchor comprises a portion of the plurality of microblades being oriented at an angle of about 90° with respect to a remaining portion of the plurality of microblades; and (vii) each one of the plurality of microblades defines essentially a plane and wherein the anchor comprises a portion of the plurality of microblades being oriented at an angle within a range of about 1° to about 89° with respect to a remaining portion of the plurality of microblades.

15. A method of transdermally sampling an agent, comprising:

a. placing a device on a body surface through which the agent is to be withdrawn, the device including a sheet having a plurality of openings therethrough and a plurality of microblades extending downward therefrom, whereby agent transmitting pathways are formed through the stratum corneum at the body surface;

b. applying a negative pressure to the pathways through the openings in the sheet, thereby withdrawing the agent through the pathways and said openings; and c. collecting the agent in a reservoir.

16. The method of claim 15, wherein the sampled agent is selected from the group consisting of body analytes, electrolytes, blood gases, illicit drugs, licit drugs and glucose.

17. The method of claim 15, further comprising:

connecting a negative pressure driven sampling device to a side opposite of a side of the sheet having the microblades extending downward therefrom, the sampling device in negative pressure applying communication with the openings in the sheet.

* * * * *

UNITED STATES PATENT AND TRADEMARK OFFICE
CERTIFICATE OF CORRECTION

| | |
|---|---|
| PATENT NO. | : 6,537,264 B1 |
| APPLICATION NO. | : 09/466819 |
| DATED | : March 25, 2003 |
| INVENTOR(S) | : Michel J.N. Cormier and Felix Theeuwes |

It is certified that error appears in the above-identified patent and that said Letters Patent is hereby corrected as shown below:

On Title page, column 1, Insert Item number 73 (Assignee:) --Alza Corporation, Mountain View, Ca--

Signed and Sealed this

Ninth Day of January, 2007

JON W. DUDAS
*Director of the United States Patent and Trademark Office*